(12) United States Patent
Akimoto et al.

(10) Patent No.: US 6,812,020 B1
(45) Date of Patent: Nov. 2, 2004

(54) PROCESS FOR PRODUCING OMEGA-9 HIGHLY UNSATURATED FATTY ACID AND LIPID CONTAINING THE SAME

(75) Inventors: Kengo Akimoto, Osaka (JP); Hiroshi Kawashima, Takatsuki (JP); Sakayu Shimizu, Kyoto (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/634,851

(22) Filed: Aug. 8, 2000

Related U.S. Application Data

(62) Division of application No. 08/917,230, filed on Aug. 25, 1997, now Pat. No. 6,150,144.

(30) Foreign Application Priority Data

Aug. 23, 1996 (JP) .............................................. 8-222612

(51) Int. Cl.⁷ .............................. C12N 1/20; C12P 7/64
(52) U.S. Cl. ..................................... 435/252.1; 435/134
(58) Field of Search ............................... 435/252.1, 134

(56) References Cited

U.S. PATENT DOCUMENTS

| | | |
|---|---|---|
| 4,916,066 A | 4/1990 | Akimoto et al. |
| 5,034,321 A | 7/1991 | Nakajima et al. |
| 5,128,250 A | 7/1992 | Akimoto et al. |
| 5,322,780 A | 6/1994 | Kawashima et al. |
| 5,376,541 A | 12/1994 | Kawashima et al. |
| 5,401,646 A | 3/1995 | Shinmen et al. |
| 5,658,767 A | 8/1997 | Kyle |
| 6,150,144 A * | 11/2000 | Akimoto et al. ............ 435/134 |

FOREIGN PATENT DOCUMENTS

| | | |
|---|---|---|
| EP | 0 252 716 | 1/1988 |
| EP | 0 535 939 | 4/1993 |
| EP | 0 790 056 | 8/1997 |

OTHER PUBLICATIONS

Computer JPAB Abstract JP403272692A Yamada et al Dec. 4, 1991.*
S. Jarenokitmongkol et al., *Journal of General Microbiology*, 138:997–1002 (1992).
M. Certik et al., *Tibtech*, 16:500–505 (1988).
Saeree Jareonkitmongkol et al, "Production of an Eicosapentaenoic Acid–Containing Oil by a Δ 12 Desaturase–Defective Mutant of *Mortierella alpina* 1S–4," JAOCS, vol. 70, No. 2, pp. 119–123, Feb. 1993.
S. Shimizu et al, "XVII *Mortierella* Species (Fungi): Production of $C_{20}$ Polyunsaturated Fatty Acids," Biotechnology in Agriculture and Forestry, vol. 33, 1995, pp. 308–325.

* cited by examiner

Primary Examiner—Herbert J. Lilling
(74) Attorney, Agent, or Firm—Burns, Doane, Swecker & Mathis, L.L.P.

(57) ABSTRACT

The present invention discloses a process for producing lipid containing omega-9 highly unsaturated fatty acid by culturing in a medium a mutant strain obtained by mutation on a microorganism having the ability to produce arachidonic acid belonging to the genus *Mortierella* and so forth, in which Δ12 desaturation activity is decreased or lost, but at least one of Δ5 desaturation activity, Δ6 desaturation activity and chain length elongation activity is elevated. Moreover, the present invention also discloses a process for producing omega-9 highly unsaturated fatty acid by collecting omega-9 highly unsaturated fatty acid from the culture or lipid described above.

40 Claims, No Drawings

US 6,812,020 B1

PROCESS FOR PRODUCING OMEGA-9 HIGHLY UNSATURATED FATTY ACID AND LIPID CONTAINING THE SAME

This application is a divisional, of application Ser. No. 08/917,230, filed Aug. 25, 1997 now U.S. Pat. No. 6,150,144.

BACKGROUND OF INVENTION

1. Field of Invention

The present invention relates to a process for producing omega-9 highly unsaturated fatty acid and lipid containing the same by fermentation using a mutant strain in which $\Delta 12$ desaturation activity has been decreased or lost, but at least one of $\Delta 5$ desaturation activity, $\Delta 6$ desaturation activity and chain length elongation activity is elevated.

2. Related Art

Omega-9 highly unsaturated fatty acids, such as 5,8,11-eicosatrienoic acid (referred to as mead acid) and 8,11-eicosadienoic acid, are known to exist as one of the constituent fatty acids of animal tissue that has become deficient in essential fatty acids. However, it has been extremely difficult to isolate and purify them since they are present in extremely small amounts. Since it is possible for these highly unsaturated fatty acids to become precursors of the leucotriene 3 group in the body, considerable expectations have been placed on their physiological activity. Their use for anti-inflammatory, anti-allergic and anti-rheumatic effects has recently been reported (Japanese Unexamined Patent Publication No. 7-41421).

There is therefore a strong desire to develop a method for producing omega-9 highly unsaturated fatty acids in large amounts. A process for producing omega-9 highly unsaturated fatty acid and lipid containing the same was previously completed by performing mutation on microorganisms having the ability to produce arachidonic acid and isolating those microorganisms in which $\Delta 12$ desaturation activity has been decreased or lost (Japanese Unexamined Patent Publication No. 5-91888). However, although it is revolutionary and significant that a process for producing omega-9 highly unsaturated fatty acid and lipid containing the same was developed since such a process had not existed in the past, there was still much room for improvement in yield. Consequently, there has been a strong desire to develop a process for efficiently producing a larger amount of omega-9 highly unsaturated fatty acids.

SUMMARY OF INVENTION

Thus, the present invention is intended to provide a process that makes it possible to produce omega-9 highly unsaturated fatty acid or lipid containing the same in a large amount using conventional inexpensive media.

As a result of various researches conducted to achieve the above-mentioned object, the inventors of the present invention found a mutant in which $\Delta 12$ desaturation activity has been decreased or lost, but at least one of $\Delta 5$ desaturation activity, $\Delta 6$ desaturation activity and chain length elongation activity has been elevated, thereby leading to completion of the present invention.

Thus, the present invention provides a process for producing lipid containing omega-9 highly unsaturated fatty acid comprising the steps of:

culturing in a medium a mutant strain obtained by mutation on a microorganism having an ability to produce arachidonic acid belonging to a genus selected from the group consisting of the genera *Mortierella, Conidiobolus, Pythium, Phytophthora, Penicillium, Cladosporium, Mucor, Fusarium, Aspergillus, Rhodotorula, Entomophthora, Echinosporangium* and *Saprolegnia*, in which $\Delta 12$ desaturation activity has been decreased or lost, but at least one of $\Delta 5$ desaturation activity, $\Delta 6$ desaturation activity and chain length elongation activity has been elevated; and, recovering lipid containing omega-9 highly unsaturated fatty acid from the culture.

Moreover, the present invention provides a process for producing an omega-9 highly unsaturated fatty acid comprising the step of recovering the omega-9 highly unsaturated fatty acid from the culture or lipid obtained according to the process described above.

DETAILED DESCRIPTION

In the present invention, the microorganisms used for mutation (to be referred to as the "parent strains") are microorganisms that have the ability to produce arachidonic acid and belong to the genus *Mortierella, Conidiobolus, Pythium, Phytophthora, Penicillium, Cladosporium, Mucor, Fusarium, Aspergillus, Rhodotorula, Entomophthora, Echinosporangium* or *Saprolegnia*.

These microorganisms convert stearic acid to oleic acid by $\Delta 9$ desaturase, oleic acid to linoleic acid by $\Delta 12$ desaturase, linoleic acid to γ-linolenic acid by $\Delta 6$ desaturase, γ-linolenic acid to dihomo-γ-linolenic acid by chain length elongation enzyme, and dihomo-γ-linolenic acid to arachidonic acid by $\Delta 5$ desaturase. In addition, these microorganisms biosynthesize 6,9-octadecadienoic acid from oleic acid by $\Delta 6$ desaturase, 8,11-eicosadienoic acid from 6,9-octadecadienoic acid by chain length elongation enzyme, and mead acid from 8,11-eicosadienoic acid by $\Delta 5$ desaturase when $\Delta 12$ desaturation activity is inhibited.

Microorganisms belonging to the subgenus Mortierella in the genus Mortierella, which exhibits excellent arachidonic acid productivity, are preferable for the parent strain used in the present invention, examples of which include the strains *Mortierella elongata* IFO 8570, *Mortierella exigua* IFO 8571, *Mortierella hygrophila* IFO 5941 and *Mortierella alpina* IFO 8568, ATCC 16266, ATCC 32221, ATCC 42430, CBS 219.35, CBS 224.37, CBS 250.53, CBS 343.66, CBS 527.72, CBS 529.72, CBS 608.70 and CBS 754.68.

All of these strains are available without restriction from the Institute of Fermentation Osaka (IFO) located in Osaka, Japan, the American Type Culture Collection (ATCC) located in the USA, or the Centraalbureau voor Schimmelcultures (CBS). In addition, the strain *Mortierella elongata* SAM0219 (FERM P-8703) (FERM BP-1239), which was isolated from the soil by the inventors of the present invention, can also be used. *Mortierella elongata* SAM 0219 was deposited as an international deposition under the Budapest Treaty as FERM BP-1239 on Mar. 19, 1986 at the Institute of Bioscience and Human-Technology Agency of Industrial Science and Technology, 1–3 Higashi 1-chome, Tsukuba-shi, Ibaraki-ken, 305, Japan.

In addition, the parent strain used in the present invention includes mutant or recombinant strains of the above-mentioned microorganisms (wild strains) having the ability to produce arachidonic acid, namely strains intentionally designed so that the content of omega-9 highly unsaturated fatty acid, the total lipid content or both is greater than the amount produced by the original wild strain when cultured using the same substrate. Moreover, said parent strain also includes microorganisms designed to produce an amount of omega-9 highly unsaturated fatty acid equal to that of the corresponding wild strain by efficiently using a substrate having excellent cost benefit.

In order to obtain a mutant of the present invention having decreased or lost Δ12 desaturation activity, but at least one of elevated Δ5 desaturation activity, Δ6 desaturation activity and chain length elongation activity, mutation is performed on the above-mentioned microorganism having the ability to produce arachidonic acid to first obtain a mutant having decreased or lost Δ12 desaturation activity. Moreover, by then mutation on this mutant strain, a mutant can be obtained in which Δ12 desaturation activity has been decreased or lost, but at least one of Δ5 desaturation activity, Δ6 desaturation activity and chain length elongation activity has been elevated. An example of a mutant that can be used having decreased or lost Δ12 desaturation activity is *Mortierella alpina* SAM1861. (FERM BP-3590). *Mortierella alpina* SAM 1861 was deposited as an international deposition under the Budapest Treaty as FERM BP-3590 on Sep. 30, 1991 at the Institute of Bioscience and Human-Technology Agency of Industrial Science and Technology, 1–3 Higashi 1-chome, Tsukuba-shi, Ibaraki-ken, 305, Japan.

By using a microorganism having decreased or lost Δ12 desaturation activity, and preferably a microorganism in which Δ12 desaturation activity is absent, for the parent in the mutant of the present invention, whether or not its Δ5 desaturation activity, Δ6 desaturation activity or chain length elongation activity is elevated can be easily evaluated.

More specifically, since omega-6 unsaturated fatty acids such as linoleic acid, γ-linolenic acid, dihomo-γ-linolenic acid and arachidonic acid are inherently either absent or only present in very small amounts in microbial cells in the case of a microorganism in which Δ12 desaturation activity has been either decreased or lost, γ-linolenic acid is formed by Δ6 desaturase if the rest cells obtained after culturing are reacted with linoleic acid, arachidonic acid is formed by Δ5 desaturase if it is reacted with dihomo-γ-linolenic acid, or dihomo-γ-linolenic acid is formed by chain length elongation enzyme if it is reacted with γ-linolenic acid. Since the activity of each enzyme can be easily assayed, Δ5 desaturation activity, Δ6 desaturation activity and chain length elongation activity of microorganisms obtained by mutation can be evaluated by comparing them with the parent strain.

Although a specific example of a mutant strain of the present invention that can be used is *Mortierella alpina* SAM086 (FERM P-15766) (which was deposited as an international deposition under the Budapest Treaty as FERM BP-6032 on Aug. 5, 1996 at the said Institute), a microorganism lack of Δ12 desaturation activity and having elevated Δ6 desaturation activity that was induced by the inventors of the present invention from *Mortierella alpina* SAM1861, such mutants are not limited to this strain, but rather any mutants can be used provided that when the Δ5 desaturation activity, Δ6 desaturation activity or chain length elongation activity of the parent strain in which Δ12 desaturation activity is decreased or lost is taken to be expressed "1", at least one of these activities exhibits a level of activity that exceeds 1.

Examples of omega-9 highly unsaturated fatty acids obtained by culturing a mutant of the present invention include 6,9-octadecadienoic acid, 8,11-eicosadienoic acid and 5,8,11-eicosatrienoic acid.

In the present invention, mead acid can be produced in a large amount by using, in particular, a mutant in which Δ12 desaturation activity has been absent, and both Δ5 desaturation activity and Δ6 desaturation activity have been elevated.

Typical mutation procedures can be performed for inducing mutation, such as by irradiating with radiation (X-rays, γ-rays or neutron beam), ultraviolet rays or heat treatment, or by suspending the microorganism in a suitable buffer, adding a mutagen and incubating for a predetermined amount of time followed by suitably diluting and growing on agar medium to obtain colonies of the mutant strain. Examples of mutagens include alkylating agents such as nitrogen mustard, methylmethane sulfonate (MMS) and N-methyl-N-nitro-N-nitrosoguanidine (NTG), base analogs such as 5-bromouracil, antibiotics such as mitomycin C, base synthesis inhibitors such as 6-mercaptopurine, pigments such as proflavin (and other derivatives), certain types of carcinogens such as 4-nitroquinoline-N-oxide, and other compounds such as manganese chloride and formaldehyde. In addition, the parent strain may in the form of growing cells (mycelium) or spores.

In order to culture a mutant in the production process of the present invention, the spores, mycelia or pre-culture liquid obtained by culturing in advance are inoculated into a liquid or solid medium. In the case of using a liquid medium, although any typically used substances can be used for the carbon source, examples of which include glucose, fructose, xylose, saccharose, maltose, soluble starch, molasses, glycerol, mannitol and citric acid, glucose, maltose, molasses and glycerol are particularly preferable.

In addition, organic nitrogen sources such as yeast extract, wheat germ extract, beef extract, casamino acids, corn steep liquor and urea, or inorganic nitrogen sources such as sodium nitrate, ammonium nitrate and ammonium sulfate can be used for the nitrogen source. In addition, phosphates such as potassium phosphate and potassium dihydrogen phosphate, inorganic salts such as ammonium sulfate, sodium sulfate, magnesium sulfate, iron sulfate, copper sulfate, magnesium chloride and calcium chloride, as well as vitamins can also be used as necessary as trace nutrients.

There are no particular limitations on the concentrations of these medium components provided they do not inhibit growth of the microorganism. In terms of practicality, the carbon source should typically be used at 0.1 to 30% by weight, and preferably 1 to 15% by weight, and the nitrogen source at 0.01 to 10% by weight, and preferably 0.1 to 5% by weight.

The culture temperature should be 5 to 40° C. and preferably 20 to 30° C., and after the microorganisms have grown by cultivation at 20 to 30° C., omega-9 highly unsaturated fatty acids can also be produced by following cultivation at 5 to 20° C. An amount of omega-9 highly unsaturated fatty acids formed in the resulting fatty acids can be increased by such a temperature control. The pH value of the medium should be 4 to 10, and preferably 5 to 8, and cultivation is performed by aerated agitation culture, shaking culture or stationary culture. Cultivation is normally performed for 2 to 20 days, preferably for 5 to 20 days and more preferably for 5 to 15 days.

In the case of using a solid culture, cultivation is performed for 3 to 14 days at a temperature of 5 to 40° C., and preferably 20 to 30° C., using wheat bran, rice chaff or rice bran containing 50 to 100% by weight of water relative to the weight of the solid substances. In this case, nitrogen sources, inorganic salts and trace nutrients can be added as necessary. In addition, in the present invention, accumulation of omega-9 highly unsaturated fatty acids can be promoted by adding a precursor of omega-9 highly unsaturated fatty acids to the medium during culturing.

Examples of this precursor include hydrocarbons such as tetradecane, hexadecane and octadecane, fatty acids, their salts (e.g., sodium salts or potassium salts) or their esters such as tetradecanoic acid, hexadecanoic acid and octadecanoic acid, or oils containing fatty acids as their constituent ingredients (e.g., olive oil, coconut oil and palm oil). This precursor is not limited to these examples, however. The total amount of the added substrate is 0.001 to 10% by weight, and preferably 0.5 to 10% by weight relative to the amount of medium. In addition, cultivation may also be performed using these precursor as the sole carbon source.

These carbon sources, nitrogen sources, inorganic salts, vitamins or substrates may be added before or immediately after inoculation with a producer microorganism, or may be added after cultivation has already been started. Alternatively, they may be added at either or both times. Addition immediately after the start of cultivation may be performed all at once or intermittently by dividing over several additions. Alternatively, addition may be performed continuously.

By cultivation in this manner, lipids containing a large amount of omega-9 highly unsaturated fatty acids will be formed and accumulate intracellularly. In the case of liquid culture, lipid containing omega-9 highly unsaturated fatty acids is recovered from the cultured medium or sterilized cultured medium from an intermediate step in the production of oil by culturing microorganisms, from the cultured medium or sterilized cultured medium at completion of cultivation, or from cultured cells or their dried product collected from any of the above cultured media. For example, lipid containing omega-9 highly unsaturated fatty acids can be recovered from cultured cells and the lipid containing omega-9 highly unsaturated fatty acids can be isolated in the manner described below.

Following completion of cultivation, the cultured cells are obtained from the cultured medium by centrifugation and/or any conventional solid-liquid separation technique such as filtration. The cells are preferably washed, crushed and dried. Drying can be performed by freeze-drying or air drying. The dried cells are preferably extracted with organic solvents in the presence of flowing nitrogen gas. Examples of organic solvents that can be used include ethyl ether, hexane, methanol, ethanol, chloroform, dichloromethane and petroleum ether, while alternating extraction with methanol and petroleum ether, and extraction using a single layer solvent of chloroform, methanol and water give good results. The organic solvent is then distilled off from the extract under reduced pressure to obtain lipid containing a high concentration of omega-9 highly unsaturated fatty acids.

In addition, extraction can also be performed using wet cells in place of the method described above. In this case, a solvent such as methanol or ethanol that is miscible with water, or mixed solvents comprising these solvents, water and/or other solvents that are miscible with water, can be used. The other parts of the procedure are the same as that described above.

The omega-9 highly unsaturated fatty acids are present in the lipid obtained in the above-mentioned manner as a triglyceride, or as a compound bonded to phosphatidyl choline, phosphatidyl ethanolamine or phosphatidyl inositol. Purification of triglyceride containing omega-9 highly unsaturated fatty acids from the lipid containing omega-9 highly unsaturated fatty acids recovered from the culture can be performed in accordance with routine methods such as hexane extraction followed by removal of free acid, decolorization, deodorization, degumming treatment or cooling separation.

In addition, omega-9 highly unsaturated fatty acids are contained in the lipid obtained in the manner described above in the form of a lipid compound, such as the constituent component of a fat. Although these can be separated directly, it is preferable to separate them in the form of an ester of a lower alcohol, examples of which include methyl 8,11-eicosadienoate, methyl 6,9-octadecadienoate and methyl ester of mead acid. By converting into esters in this manner, these components can be easily separated from other lipid components. in addition, they can also be easily separated from other fatty acids formed.during cultivation, such as palmitic acid and oleic acid (these are also esterified during esterification of omega-9 highly unsaturated fatty acids). For example, in order to obtain the methyl ester of omega-9 highly unsaturated fatty acids, it is preferable to treat the above-mentioned extracted lipid for 1 to 24 hours at room temperature with 5 to 10% methanolic HCl acid or 10 to 50% BF3-methanol.

In order to recover omega-9 highly unsaturated fatty acids from the above-mentioned treatment solution, it is preferable to extract with an organic solvent such as hexane, ethyl ether or ethyl acetate. Next, by drying this extract over anhydrous sodium sulfate and so forth and distilling off the organic solvent preferably under reduced pressure, a mixture is obtained that consists mainly of fatty acid esters. This mixture contains methyl palmitate, methyl stearate, methyl oleate and other fatty acid methyl esters in addition to the target omega-9 highly unsaturated fatty acid methyl esters. In order to isolate omega-9 highly unsaturated fatty acid methyl esters from the mixture of fatty acid methyl esters, column chromatography, low-temperature crystallization, urea inclusion or liquid-liquid counter-current distribution chromatography and so forth can be used alone or in combination.

In order to obtain omega-9 highly unsaturated fatty acids from the various types of omega-9 highly unsaturated fatty acid methyl esters isolated in the manner described above, after hydrolysis in the presence of alkali, the mixture should be extracted with an organic solvent such as ethyl ether or ethyl acetate.

In addition, in order to recover the omega-9 highly unsaturated fatty acids without going through their methyl ester, after hydrolysis of the above-mentioned extracted lipid with alkali (by, for example, treating for 2 to 3 hours at room temperature with 5% sodium hydroxide solution), the omega-9 highly unsaturated fatty acids can be extracted and purified from the hydrolysate by methods commonly used for extraction and purification of fatty acids.

EXAMPLES

The following Examples provide a detailed explanation of the present invention.

Example 1

*Mortierella alpina* SAM1861, a mutant lack of $\Delta 12$ desaturation activity, was inoculated into Czapek agar medium (0.2% $NaNO_3$, 0.1% $K_2HPO_4$, 0.05% $MgSo_4$, 0.05% KCl, 0.001% $FeSO_4$, 3% sucrose, 2% agar, pH 6.0) to form spores to prepare a spore solution (50 mM Tris/malate buffer (pH 7.5), $1\times10^6$ spores/ml).

0.5 ml of 100 mM Tris/malate buffer (pH 7.5) were added to 1.0 ml of the resulting spore solution followed by the addition of 500 $\mu$l of NTG solution (5 mg of N-methyl-N-nitro-N-nitrosoguanidine/1 ml of deionized water) and incubating for 15 minutes at 28° C. to perform mutation treatment.

The NTG-treated spore suspension was diluted to roughly $10^{-3}$ to $10^{-4}$ and applied to a GY agar plate (1%. glucose, 0.5% yeast extract, 0.005% Triton X-100, 1.5% agar, pH 6.0). Those colonies that appeared during culturing at 28° C. were randomly picked up and transferred to a new plate.

The picked storage colonies were cultured for 2 days at 28° C. and 2 days at 12° C. on a GY agar plate and then excised while still attached to the agar and dried at 100° C.

The resulting dried cells were placed in a screw-cap test tube (16.5 mm in diameter) followed by methyl-esterification by treating for 3 hours at 50° C. by adding 1 ml of methylene chloride and 2 ml of 10% methanolic HCl. After adding 4 ml of n-hexane and 1 ml of water, extracting two times, and distilling off the solvent from the extract using a centrifugal evaporator (40° C., 1 hour), the resulting fatty acid methyl esters were analyzed by gas chromatography. The results are shown in Table 1.

SAM2086, induced by mutation from SAM1861, was clearly shown to demonstrate both excellent mead acid productivity and containing ratio.

TABLE 1

| Strain | Growth (g/l)* | ω9 PUFA Production (g/l)** | | | Fatty Acid Composition (%)+ | | | | | | | | | | | | | |
|---|---|---|---|---|---|---|---|---|---|---|---|---|---|---|---|---|---|---|
| | | 18:2 (ω9) | 20:2 (ω9) | 20:3 (ω9) | 16:0 | 18:0 | 18:1 | LA | 18:2 (ω9) | GLA | 20:1 | 20:2 (ω9) | 20:3 (ω9) | DGLA | Ara | EPA | 24:0 | Other |
| SAM1861 | 19.94 | 1.27 | 0.32 | 1.61 | 6.61 | 7.74 | 41.23 | 0 | 12.94 | 0 | 2.26 | 3.29 | 16.43 | 0 | 0 | 0 | 4.58 | 4.92 |
| SAM2086 | 18.49 | 1.10 | 0.31 | 1.84 | 6.96 | 6.88 | 38.51 | 0 | 12.41 | 0 | 2.19 | 3.53 | 20.87 | 0 | 0 | 0 | 3.80 | 4.85 |

+LA: linoleic acid, 18:2 (ω9): 6,9-octadecadienoic acid, GLA: γ-linolenic acid, 20:2 (ω9): 8,11-eicosadienoic acid, 20:3 (ω9): mead acid, DGLA: dihomo-γ-linolenic acid, Ara: arachidonic acid, EPA: eicosapentaenoic acid
*Dry cell weight per liter of medium
**Weight of omega-9 unsaturated fatty acids per liter of medium After adding 4 ml of n-hexane and 1 ml of water, extracting two times, and distilling off the solvent from the extract using a centrifugal evaporator (40° C., 1 hour), the resulting fatty acid methyl esters were analyzed by capillary gas chromatography. As a result of screening, *Mortierella alpina* SAM2086 (FERM P-15766) was obtained having higher mead acid productivity than the parent strain, *Mortierella alpina* SAM1861. *Mortierella alpina* SAM 2086 was deposited as FERM P-15766 on Aug. 5, 1996 at the Institute of Bioscience and Human-Technology Agency of industrial Science and Technology, 1–3 Higashi 1-chome, Tsukuba-shi, Ibaraki-ken, 305, Japan. Moreover, *Mortierella alpina* SAM2104 was obtained by performing similar mutation treatment as that described above using SAM2086 for the parent strain.

Example 2

Five liters of medium (pH 6.0) containing 4% glucose and 1% yeast extract was placed in a 10 liter jar fermentor and sterilized for 30 minutes at 120° C. The medium was then inoculated with 100 ml of a preculture of mutant SAM1861 or SAM2086 of *Mortierella alpina* followed by aerated agitation culture for 8 days with aeration at one volume/volume/min. and agitation at 300 rpm. The culture temperature at the start of culturing was 28° C. and then lowered to 20° C. on the 2nd day of culturing. 1% Glucose was added daily from the 1st to 4th days of culturing. Following completion of culturing, the cells were recovered by filtration and after adequately washing, the resulting wet cells were freeze-dried to obtain 99.7 g and 92.5 g of dried cells for each strain, respectively.

When lipid was extracted from these dried cells according to the extraction method of Blight & Dyer using a single layer solvent of chloroform, methanol and water, lipids were obtained in the amounts of 48.92 g and 44.17 g, respectively. In order to confirm the fatty acid composition of these lipids, 10 mg of lipid was placed in screw-cap test tubes and methyl-esterified by treating for 3 hours at 50° C. by adding 1 ml of methylene chloride and 2 ml of 10% methanolic HCl. After adding 4 ml of n-hexane and 1 ml of water, extracting two times, and distilling off the solvent from the extract using a centrifugal evaporator (40° C., 1 hour), the resulting fatty acid methyl esters were analyzed by gas chromatography. The results are shown in Table 1.

Example 3

1 ml of 0.1 M phosphate buffer (pH 7.4), 30 mg of wet cells obtained in Example 2 of mutant SAM1861 or SAM2086 of *Mortierella alpina* and 100 μl of BSA suspended substrate solution (prepared by mixing 20 mg of linoleic acid, γ-linolenic acid or dihomo-γ-linolenic acid in 2 ml of 5% bovine serum albumin (fatty acid-free BSA, Sigma) and suspending by sonication for approximately 20 minutes) were added to screw-cap test tubes (16.5 mm in diameter) after which the test tubes were capped with a silicone stopper and shaken at 28° C. and 120 rpm. The reaction was stopped after 0, 2, 6 or 20 hours by adding 4 ml of ethanol.

After drying with a centrifugal evaporator (40° C., 1 hour), methyl-esterification was performed in the same manner as Example 2, and the resulting fatty acid methyl esters (substrates and reaction products) were analyzed by capillary gas chromatography. In this analysis, the same amount of 5% BSA solution was used as control. Thus, if dihomo-γ-linolenic acid is used for the substrate, Δ5 desaturation activity is determined from the amount of the reaction product, i.e., arachidonic acid; if γ-linolenic acid is used for the substrate, chain length elongation activity is determined from the amount of the reaction product, i.e., dihomo-γ-linolenic acid, and Δ5 desaturation activity is determined from the amount of arachidonic acid; and if linoleic acid is used for the substrate, Δ6 desaturation activity is determined from the amount of the reaction product, i.e., γ-linolenic acid, chain length elongation activity is determined from the amount of dihomo-γ-linolenic acid, and Δ5 desaturation activity is determined from the amount of arachidonic acid. Those results are shown in Table 2.

In the case of taking the activity of SAM1861 to be 1 for the Δ5 desaturation activity using dihomo-γ-linolenic acid for the substrate, the activity of SAM2086 was 1.74. In the case of taking the activity of SAM1861 to be 1 for the Δ6 desaturation activity using linoleic acid for the substrate, the activity of SAM2086 was 1.42. The increases in mead acid productivity and ratio of SAM2086 induced by mutation from SAM1861 of Example 2 were clearly the result of increased Δ5 desaturation activity and Δ6 desaturation activity.

Table 2 Reaction Rates of SAM1861 and SAM2086 (nmol/30 mg wet cells/hour)

| Strain | Substrate DGLA Product Ara (Δ5 DS) | Substrate GLA Product DGLA (EL) | Substrate LA Product GLA (Δ6 DS) |
|---|---|---|---|
| SAM1861 | 0.85 | 7.50 | 11.01 |
| SAM2086 | 1.45 | 6.60 | 15.6 |
| SAM2104 | 4.92 | 8.67 | 18.6 |

LA: linoleic acid, GLA: γ-linolenic acid,
DGLA: dihomo-γ-linolenic acid, Ara: arachidonic acid
Δ5 DS: Δ5 desaturation activity
Δ6 DS: Δ6 desaturation activity
EL: chain length elongation activity Example 4

2 ml of medium (pH 6.0) containing 2% glucose, 1% yeast extract and 0.5% of each of the precursors of the omega-9 highly unsaturated fatty acids indicated in Table 3, or oils containing the same, was placed in 10 ml Erlenmeyer flasks and sterilized for 20 minutes at 120° C. The flasks were each inoculated with a piece of cells of mutant SAM2086 of *Mortierella alpina* followed by culturing for 8 days at 28° C. using a reciprocating shaker (110 rpm). The results are shown in Table 3.

TABLE 3

| | Amount of Omega-9 Highly Unsaturated Fatty Acids Produced (g/l) | | |
|---|---|---|---|
| Added Substance | 18:2 | 20:2 | 20:3 |
| No addition | 0.23 | 0.04 | 0.27 |
| Hexadecane | 0.32 | 0.06 | 0.39 |
| Octadecane | 0.38 | 0.06 | 0.48 |
| Palmitic acid | 0.40 | 0.07 | 0.51 |
| Stearic acid | 0.47 | 0.07 | 0.58 |
| Oleic acid | 0.57 | 0.11 | 0.70 |
| Sodium palmitate | 0.35 | 0.08 | 0.44 |
| Sodium stearate | 0.37 | 0.08 | 0.46 |
| Sodium oleate | 0.49 | 0.09 | 0.60 |
| Methyl palmitate | 0.45 | 0.10 | 0.57 |
| Methyl stearate | 0.52 | 0.11 | 0.64 |
| Methyl oleate | 0.66 | 0.16 | 0.81 |
| Ethyl oleate | 0.67 | 0.15 | 0.82 |
| Palm oil | 0.45 | 0.08 | 0.56 |
| Olive oil | 0.48 | 0.12 | 0.58 |
| Coconut oil | 0.36 | 0.07 | 0.41 |

18:2; 6,9-octadecadienoic acid
20:2; 8,11-eicosadienoic acid
20:3; 5,8,11-eicosatrienoic acid (mead acid)

Example 5

Five liters of medium (pH 6.0) containing 2% glucose, 1% yeast extract, 0.1% olive oil and 0.01% Adecanol (defoaming agent; Trademark) was placed in a 10 liter jar fermentor followed by sterilization for 30 minutes at 120° C. 100 ml of a preculture of *Mortierella alpina* SAM2104 was inoculated. Cultivation was carried out for 8 days with aeration at 1 volume/volume/min. and agitation at 300 rpm.

The culture temperature was 28° C. at the start of culturing and then lowered to 20° C. starting on the 2nd day of culturing. 1.5% glucose was added on the 2nd and 3rd days of culturing. Following completion of culturing, 15.80 g of dried cells was obtained per liter of medium by following the same procedure as that of Example 2. The lipid was extracted in the same manner as Example 2, said lipids were methyl-esterified, the resulting fatty acid methyl esters were analyzed by gas chromatography. The amounts produced and percentages of mead acid, 8,11-eicosadienoic acid and 6,9-octadecadienoic acid relative to the total amount of fatty acids were 1.76 g/liter and 23.76% for mead acid, 0.35 g/liter and 4.75% for 8,11-eicosadienoic acid, and 0.84 g/liter and 11.35% for 6,9-octadecadienoic acid, respectively.

What is claimed is:

1. An isolated microorganism produced by the process of mutating a microorganism at least once,
which microorganism
produces arachidonic acid and
belongs to the genus *Mortierella* and a species selected from the group consisting of *Mortierella elongata, Mortierella exiqua, Mortierella hygrophila* and *Mortierella alpina*,
wherein said mutated microorganism
has decreased or lost Δ12 desaturation activity,
has at least one of Δ5 desaturation activity, Δ6 desaturation activity or chain length elongation activity elevated in comparison with said corresponding activity of the microorganism which is subject to mutation, and
produces at least about 27% more mead acid compared to the microorganism which is subject to mutation.

2. An isolated mutant microorganism according to claim 1, wherein said mutated microorganism produces about 27% more mead acid compared to the microorganism which is subject to mutation.

3. An isolated microorganism produced by the process of mutating a microorganism at least once
which microorganism
produces arachidonic acid and
belongs to the genus *Mortierella* and a species selected from the group consisting of *Mortierella elongata, Mortierella exiqua, Mortierella hygrophila* and *Mortierella alpina*,
wherein said mutated microorganism
has decreased or lost Δ12 desaturation activity, and
has Δ5 desaturation activity elevated by at least about 74% in comparison with said corresponding activity of the microorganism which is subject to mutation.

4. An isolated mutant microorganism according to claim 3, wherein said Δ5 desaturation activity is elevated by about 74% in comparison with said corresponding activity of the microorganism which is subject to mutation.

5. An isolated mutant microorganism according to claim 3, wherein said Δ5 desaturation activity is elevated by about 232% in comparison with said corresponding activity of the microorganism which is subject to mutation.

6. An isolated mutant microorganism according to claim 3, wherein said Δ5 desaturation activity is elevated by about 407% in comparison with said corresponding activity of the microorganism which is subject to mutation.

7. An isolated mutant microorganism according to claim 3, wherein the mutant microorganism has an increase in production of mead acid over its parent strain of at least about 27%.

8. An isolated mutant microorganism according to claim 3, wherein Δ6 desaturation activity is elevated in comparison with said corresponding activity of the microorganism which is subject to mutation.

9. An isolated mutant microorganism according to claim 3, wherein chain length elongation activity is elevated in comparison with said corresponding activity of the microorganism which is subject to mutation.

10. An isolated microorganism produced by the process of mutating a microorganism at least once
which microorganism
produces arachidonic acid and
belongs to the genus *Mortierella* and a species selected from the group consisting of *Mortierella elongata, Mortierella exiqua, Mortierella hygrophila* and *Mortierella alpina*,
wherein said mutated microorganism
has decreased or lost Δ12 desaturation activity, and
has Δ6 desaturation activity elevated by at least about 19% in comparison with said corresponding activity of the microorganism which is subject to mutation.

11. An isolated mutant microorganism according to claim 10, wherein said Δ6 desaturation activity is elevated by about 19% in comparison with said corresponding activity of the microorganism which is subject to mutation.

12. An isolated mutant microorganism according to claim 10, wherein said Δ6 desaturation activity is elevated by about 42% in comparison with said corresponding activity of the microorganism which is subject to mutation.

13. An isolated mutant microorganism according to claim 10, wherein said Δ6 desaturation activity is elevated by about 68% in comparison with said corresponding activity of the microorganism which is subject to mutation.

14. An isolated mutant microorganism according to claim 10, wherein the mutant microorganism has an increase in production of mead acid over its parent strain of at least about 27%.

15. An isolated mutant microorganism according to claim 10, wherein Δ5 desaturation activity is elevated in comparison with said corresponding activity of the microorganism which is subject to mutation.

16. An isolated mutant microorganism according to claim 10, wherein chain length elongation activity is elevated in comparison with said corresponding activity of the microorganism which is subject to mutation.

17. An isolated microorganism produced by the process of mutating a microorganism at least once
which microorganism
produces arachidonic acid and
belongs to the genus Mortierella and a species selected from the group consisting of *Mortierella elongata, Mortierella exiqua, Mortierella hygrophila* and *Mortierella alpina*,
wherein said mutated microorganism
has decreased or lost Δ12 desaturation activity, and
has chain length elongation activity elevated by at least about 15% in comparison with said corresponding activity of the microorganism which is subject to mutation.

18. An isolated mutant microorganism according to claim 17, wherein said chain length elongation activity is elevated by about 31% in comparison with said corresponding activity of the microorganism which is subject to mutation.

19. An isolated mutant microorganism according to claim 17, wherein the microorganism belongs to the species *Mortierella elongata*.

20. An isolated mutant microorganism according to claim 17, wherein the microorganism belongs to the species *Mortierella alpina*.

21. An isolated mutant microorganism according to claim 20, wherein the mutant microorganism is SAM 2086.

22. An isolated mutant microorganism according to claim 19, wherein the mutant microorganism is derived from *Mortierella elongata* SAM 0219.

23. An isolated mutant microorganism according to claim 20, wherein the mutant microorganism is derived from *Mortierella alpina* SAM 1861.

24. An isolated mutant microorganism according to claim 17, wherein the mutant microorganism has an increase in production of mead acid over its parent strain of at least about 27%.

25. An isolated mutant microorganism according to claim 17, wherein the mutant microorganism has an increase in production of mead acid over its parent strain of about 27%.

26. An isolated microorganism according to claim 1, wherein the microorganism belongs to the species *Mortierella elongata*.

27. An isolated microorganism according to claim 1, wherein the microorganism belongs to the species *Mortierella alpina*.

28. An isolated microorganism according to claim 27, wherein the mutant microorganism is SAM 2086.

29. An isolated microorganism according to claim 26, wherein the microorganism is derived from *Mortierella elongata* SAM 0219.

30. An isolated microorganism according to claim 27, wherein the mutant microorganism is derived from *Mortierella alpina* SAM 1861.

31. An isolated mutant microorganism according to claim 3, wherein the microorganism belongs to the species *Mortierella elongata*.

32. An isolated mutant microorganism according to claim 3, wherein the microorganism belongs to the species *Mortierella alpina*.

33. An isolated mutant microorganism according to claim 32, wherein the mutant microorganism is SAM 2086.

34. An isolated mutant microorganism according to claim 10, wherein the microorganism belongs to the species *Mortierella elongata*.

35. An isolated mutant microorganism according to claim 10, wherein the microorganism belongs to the species *Mortierella alpina*.

36. An isolated mutant microorganism according to claim 35, wherein the mutant microorganism is SAM 2086.

37. An isolated mutant microorganism according to claim 34, wherein the mutant microorganism is derived from *Mortierella elongata* SAM 0219.

38. An isolated mutant microorganism according to claim 35, wherein the mutant microorganism is derived from *Mortierella alpina* SAM 1861.

39. An isolated mutant microorganism according to claim 31, wherein the mutant microorganism is derived from *Mortierella elongata* SAM 0219.

40. An isolated mutant microorganism according to claim 32, wherein the mutant microorganism is derived from *Mortierella alpina* SAM 1861.

* * * * *